United States Patent [19]

Moon et al.

[11] 4,008,217
[45] Feb. 15, 1977

[54] 1'-VARIABLE-1',1'-DIHALO-HALOBENZENEAZOMETHANES

[75] Inventors: Malcolm W. Moon, Kalamazoo; Victor L. Rizzo, Paw Paw, both of Mich.

[73] Assignee: The Upjohn Company, Kalamazoo, Mich.

[22] Filed: Nov. 5, 1975

[21] Appl. No.: 629,014

Related U.S. Application Data

[60] Continuation of Ser. No. 468,767, May 10, 1974, abandoned, which is a division of Ser. No. 138,269, April 28, 1971, Pat. No. 3,834,892.

[52] U.S. Cl. .................. 260/192; 71/121; 260/193; 260/544 N; 424/226
[51] Int. Cl.$^2$ ............... A01N 9/24; C07C 107/00
[58] Field of Search ..................... 260/192

[56] References Cited

UNITED STATES PATENTS

| | | | |
|---|---|---|---|
| 3,186,824 | 6/1965 | Flenner | 260/192 |
| 3,282,912 | 11/1966 | Benzing | 260/158 |
| 3,390,146 | 6/1968 | Nield et al. | 260/192 |
| 3,629,227 | 12/1971 | Meckel et al. | 260/174 |
| 3,830,797 | 8/1974 | Macleay et al. | 260/192 |

FOREIGN PATENTS OR APPLICATIONS

| | | | |
|---|---|---|---|
| 1,310,240 | 10/1962 | France | 260/192 |
| 1,312,732 | 11/1962 | France | 260/192 |

Primary Examiner—Floyd D. Higel
Attorney, Agent, or Firm—John J. Killinger; Roman Saliwanchik

[57] ABSTRACT

1'-variable-1',1'-dihalo-halobenzeneazomethanes of the structural formula:

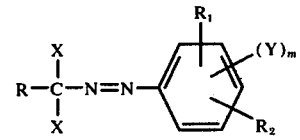

wherein R is hydrogen; alkyl of from 1 to 7 carbon atoms, inclusive; cycloalkyl of from 3 to 7 carbon atoms, inclusive; haloalkyl of from 1 to 7 carbon atoms, inclusive; halocycloalkyl of from 3 to 7 carbon atoms, inclusive; alkoxyalkyl of from 2 to 8 carbon atoms, inclusive; hydroxyalkyl of from 1 to 7 carbon atoms, inclusive; and phenyl optionally having 1, 2, or 3 substituents, e.g., halogen atoms, lower-alkyl or from 1 to 4 carbon atoms, inclusive, halolower-alkyl of from 1 to 4 carbon atoms, inclusive, and lower-alkoxy of from 1 to 4 carbon atoms, inclusive; the X's are independently bromine, chlorine, or fluorine; m is an integer 0, 1, 2, or 3; and $R_1$, $R_2$, and Y are independently halogen, lower-alkyl of from 1 to 4 carbon atoms, inclusive; halolower-alkyl of from 1 to 4 carbon atoms, inclusive; or lower-alkoxy of from 1 to 4 carbon atoms, inclusive; providing however, that at least one $R_1$ and $R_2$ is halogen, and that the sum of the carbon atoms in substituents $R_1$, $R_2$, and Y may not be more than 15. The compounds are active as herbicides and are formulated in agricultural formulations for use as herbicides.

19 Claims, No Drawings

1'-VARIABLE-1',1'-DIHALO-HALOBENZENEAZOMETHANES

CROSS REFERENCE TO RELATED APPLICATIONS

This application is a continuation of application Ser. No. 468,767, filed May 10, 1974, now abandoned, which in turn is a division of our co-pending application Ser. No. 138,269, filed Apr. 28, 1971 now U.S. Pat. No. 3,834,892, issued Sept. 10, 1974.

SUMMARY OF INVENTION

This invention pertains to new organic chemical compounds, a process for preparing the same, a new method for controlling weeds, and new formulations for use in controlling weeds. The invention is more particularly directed to new 1'-variable-1',1'-dihalo-halobenzeneazomethanes, a new process for preparing the same, a new method for controlling weeds therewith, and new formulations comprising 1'-variable-1',1'-dihalo-halobenzeneazomethanes for use against undesirable plants.

The new 1'-variable-1',1'-dihalo-halobenzeneazomethanes of this invention have the general structural formula:

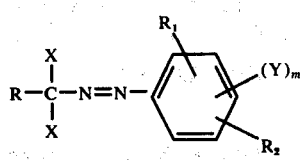

wherein R is hydrogen; alkyl of from 1 to 7 carbon atoms, inclusive; cycloalkyl of from 3 to 7 carbon atoms, inclusive; haloalkyl of from 1 to 7 carbon atoms, inclusive; halocycloalkyl of from 3 to 7 carbon atoms, inclusive; alkoxyalkyl of from 2 to 8 carbon atoms, inclusive; hydroxyalkyl of from 1 to 7 carbon atoms, inclusive; and phenyl, optionally having 1, 2, or 3 substituents, e.g., halogen atoms, lower-alkyl of from 1 to 4 carbon atoms, inclusive, halolower-alkyl of from 1 to 4 carbon atoms, inclusive, and lower-alkoxy of from 1 to 4 carbon atoms, inclusive; the X's are independently chlorine, bromine, or fluorine; m is an integer 0, 1, 2, or 3; and $R_1$, $R_2$, and Y are independently selected from halogen; lower-alkyl of from 1 to 4 carbon atoms, inclusive; halolower-alkyl of from 1 to 4 carbon atoms, inclusive; or lower-alkoxy of from 1 to 4 carbon atoms, inclusive, providing however, that at least one of $R_1$ and $R_2$ is halogen, and that the sum of the carbon atoms in substituents $R_1$, $R_2$, and Y may not be more than 15.

DETAILED DESCRIPTION OF THE INVENTION

The new 1'-variable-1',1'-dihalo-halobenzeneazomethanes of this invention (compounds according to Formula I) are prepared by vigorous halogenation procedures. More particularly, the compounds are prepared, for example, by halogenating an appropriate alkanaldehyde phenylhydrazone, a cycloalkanaldehyde phenylhydrazone, a benzaldehyde phenylhydrazone, a 2-oxoalkanoic acid 2-phenylhydrazone, an alkanoyl halide phenylhydrazone, a polymethylenecarboxyl halide phenylhydrazone, or a benzoyl chloride phenylhydrazone. A representative preferred strong halogenation procedure is to react elemental chlorine or bromine with an alkanaldehyde phenylhydrazone or an alkanoyl halide phenylhydrazone.

Illustratively, a reaction can be effected between elemental chlorine and an alkanaldehyde phenylhydrazone in the presence of a liquid reaction medium. Optimally, the reaction temperature is in the range of minus 10° C. to minus 50° C. up to about 50° C. Suitable liquid reaction media include chloroform, carbon tetrachloride, trichlorofluoromethane, methylene chloride, benzene, technical hexane, and acetic acid. The reaction medium is not critical so long as the reactants have practical limits of solubility therein and the medium is not reactive itself with the reactants. Cheapness, ease of removal by evaporation, and recoverability are considerations pertinent to selection of a reaction medium. The reaction temperature is not critical, but convenience in handling halogenating agents dictates preferences.

The new compounds are recovered from the reaction mixture by conventional techniques including filtration, solvent evaporation, distillation, chromatography, and crystallization. In the simplest situation, the desired 1'-variable-1',1'-dihalo-halobenzeneazomethane separates as a solid from the reaction mixture and is recovered on a filter. Purification is then accomplished by washing the filter cake with an appropriate liquid and recrystallizing the solids from a suitable solvent. Representative solvents for crystallization are petroleum ether, methanol, ethanol, and mixtures of benzene and technical hexane.

On the other hand, most of the compounds of this invention are colored liquids and these are readily purified by chromatographic techniques. For example, the reaction medium is removed by evaporation and the red oil thus obtained is dissolved in an organic liquid and passed through a chromatographic substrate, e.g., silica gel. Various organic liquids can be used for development of the chromatogram, a representative suitable one is a 1:9 mixture of benzene and technical hexane (parts are by volume). A 1:3 mixture is also suitable. The liquid compounds of this invention may also be purified by distillation at a reduced pressure. The reduced pressure is necessary as the compounds decompose with evolution of nitrogen at a temperature of about 250° C.

Further illustratively, halogenation of, e.g., an alkanaldehyde phenylhydrazone, a benzaldehyde phenylhydrazone, a cycloalkyl carbonyl halide (e.g., chloride) phenylhydrazone, or a 2-oxoalkanoic acid 2-phenylhydrazone can be effected with organic hypohalites. For example, trifluoromethyl hypofluorite can be reacted with an alkanoyl chloride phenylhydrazone. This reaction is advantageously effected at low temperatures, e.g., −20° C. to −60° C. although slightly higher and even lower temperatures can be used. The desired products are recovered and purified by the same conventional techniques mentioned above and known in the art.

The starting compounds for the process of this invention, e.g., alkanaldehyde phenylhydrazones, 2-oxoalkanoic acid 2-phenylhydrazones, alkanoyl halide phenylhydrazones, cycloalkyl carbonyl halide phenylhydrazones, benzoyl chloride phenylhydrazones, and others indicated by Formula I and the foregoing description are known compounds or they can be readily prepared by well-known methods. Illustratively, an alkanaldehyde can be reacted with a phenylhydrazine according to the method described by E. Fischer, Chem. Ber. 29, page 794 (1896) to obtain alkanaldehyde phenylhydrazones.

Alkanoyl halide phenylhydrazone starting compounds are readily prepared by reacting an alkanaldehyde phenylhydrazone prepared as above with a halogenating agent according to the method described by J. E. Humphries, H. Humble, and R. Evans, J. Chem. Soc. 127, p. 1304 (1925).

Alkanoyl halide phenylhydrazones are also prepared by reacting an alkanoic acid phenylhydrazide with phosphorus pentachloride.

The alkanoic acid phenylhydrazide starting compounds are known or can be readily prepared by known methods. According to one method an alkanoyl chloride is reacted with a phenylhydrazine, using the procedures described by J. Hausknecht, Chem. Ber. 22, p. 324 (1889), and E. Bamberger and W. Pemsel, Chem. Ber. 36, p. 359 (1903). Another method described in U.S. Pat. No. 2,912,461, issued Nov. 10, 1959, can be utilized to react an alkanoate ester and a phenylhydrazine. Still another method described by W. Autenrieth and G. Thomae, Chem. Ber. 57, p. 423 (1924) can be used to react an alkanoic acid anhydride with a phenylhydrazine and produce the corresponding alkanoic acid phenylhydrazide.

An alternative synthesis for the compounds of this invention according to Formula I wherein at least one of $R_1$ and $R_2$ are halogen is by reaction of an acyl or benzoyl halophenyldiimide with a phosphorous halide, for example phosphorus pentachloride in an inert solvent, for example carbon tetrachloride, at a temperature of between 25° C. and the reflux temperature of the solution. The acyl or benzoyl halophenyldiimide starting compounds are prepared by oxidation of an alkanoic acid halophenylhydrazide or benzoic acid halophenylhydrazide using the methods as described by R. Pütter in Methoden der Organischen Chemie (Houben Weil)-10, part 3, pp. 616–9 (1967). This method is particularly useful when compounds of the invention with a hydrogen substituent at a 2,4- or 6-position in the benzene ring are to be synthesized, for example, in the synthesis of 1',1',2, 4-tetrachlorobenzeneazopropane Referring to general Formula I and the variables R, X, $R_1$, $R_2$, Y and m specified therein some representative variations can be indicated.

In particular, R being alkyl of from 1 to 7 carbon atoms, inclusive, means methyl, ethyl, propyl, butyl, pentyl, hexyl, heptyl, and isomeric forms thereof. Similarly, cycloalkyl of from 3 to 7 carbon atoms, inclusive, means cyclopropyl, cyclobutyl, cyclopentyl, cyclohexyl, alkyl substituted forms thereof, and cycloheptyl.

Hydroxyalkyl of from 1 to 7 carbon atoms, inclusive, includes for example, hydroxymethyl, 2-hydroxyethyl, 3-hydroxypropyl, 4-hydroxybutyl, 5-hydroxypentyl, 6-hydroxyhexyl, 7-hydroxyheptyl, and the various branched chain and hydroxy-position isomers thereof including, without reservation, closely related polyhydroxy radicals, e.g., 3,4-dihydroxybutyl.

Alkoxyalkyl of from 2 to 8 carbon atoms, inclusive, includes, for example, methoxymethyl, 2-methoxyethyl, 3-methoxypropyl, n-butoxyethyl, n-propoxyamyl, 6-ethoxyhexyl, α-methoxyisobutyl, and the various homologues and isomers thereof. Lower-alkoxy of from 1 to 4 carbon atoms, inclusive, follows a like variation of alkoxy groups.

Haloalkyl of from 1 to 7 carbon atoms, inclusive, includes, for example, chloromethyl, iodomethyl, bromomethyl, fluoromethyl, 3-chloroheptyl, trifluoromethyl, 2-chloroethyl, 2,2-difluoroethyl, 2,2-diiodoethyl, 3-chloropropyl, 2-bromopropyl, iodoisopropyl, 1,3,3-trichlorobutyl, 1,3,3-tribromoheptyl, and other halogenated straight and branched chain alkyl of from 1 to 7 carbon atoms, inclusive. Halolower-alkyl of from 1 to 4 carbon atoms, inclusive, follows the same variations.

Halocycloalkyl of from 3 to 7 carbon atoms, inclusive, includes for example, cyclopropyl chloride, cyclobutyl bromide, cyclopentyl chloride, cyclohexyl chloride, cyclohexyl-1,3-dibromide, 4-methylcyclohexyl bromide, and cycloheptyl bromide (suberyl bromide).

Substituted phenyl groups R include for example, p-tolyl, 2,5-xylyl, p-anisyl, p-phenethyl, p-chlorophenyl, 3,4-dichlorophenyl, 2,5-dichlorophenyl, p-fluorophenyl, m-chlorophenyl, o-chlorophenyl, p-isopropylphenyl, p-iodophenyl, p-bromophenyl, p-ethoxyphenyl, 5-chloro-o-anisyl, p-butoxyphenyl, p-tert-.butylphenyl, 5-ethyl-o-anisyl, and the like.

PREPARATION I

Part A.

Isobutyraldehyde phenylhydrazone

To a solution consisting of 7.2 g. (0.1 mole) isobutyraldehyde in 150 ml. chloroform was added, with stirring, 10.8 g. (0.1 mole) phenylhydrazine. The reaction flask was covered with aluminum foil and nitrogen gas was passed into the sealed flask during the reaction. The reaction mixture was stirred for 1 hr., and then heated in order to remove, by distillation, the water produced by the reaction. About 50 ml. of a water:-chloroform azeotrope was collected. Enough carbon

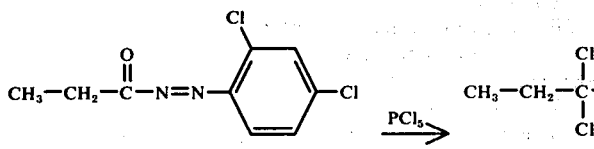 

tetrachloride was then added to bring the reaction mixture back to its original volume, thus producing a chloroform:carbon tetrachloride solution of isobutyraldehyde phenylhydrazone.

Part B

Isobutyryl chloride (2,4-dichlorophenyl)hydrazone

The chloroform:carbon tetrachloride solution of isobutyraldehyde phenylhydrazone prepared in Part A, above, was diluted to a volume of 300 ml. with carbon tetrachloride, and the air in the flask was replaced with nitrogen gas before about 14 ml. chlorine (0.3 mole) was introduced into the reaction mixture. The chlorine is introduced as a liquid in an open ended vessel from which it volatilizes to mix with and react with the isobutyraldehyde phenylhydrazone. The mixture was stirred and kept cool (below 5° C.). After ½ hr., a sample of the reaction mixture assayed by thin layer chromatography (on silica gel with technical hexane — a mixture of isomeric hexanes boiling at 142° to 156° Fahrenheit) showed no starting material present. The reaction mixture was filtered, and the solvents were removed from the filtrate by evaporation. The residue thus obtained was dissolved in 250 ml. technical hexane and the solution was poured over a column of silica gel (1365 g.). Elution of the column with technical hexane and evaporation of the solvent from the eluate gave 4.0 g. of isobutyryl chloride (2,4-dichlorophenyl)hydrazone as a light red oil.

Analysis:Calc'd. for $C_{10}H_{11}Cl_3N_2$: C, 45.22; H, 4.17; Cl, 40.05; N, 10.55. Found: C, 45.59; H, 4.42; Cl, 40.26; N, 10.02.

Preparation II

Following the procedure of Preparation I, Part A, but substituting (2,4,6-trichlorophenyl)hydrazine, o-tolylhydrazine, m-tolylhydrazine, p-tolylhydrazine, (2-bromophenyl)-hydrazine, (4-iodophenyl)hydrazine, (4-trifluoromethylphenyl)hydrazine, (3-isopropylphenyl)hydrazine, (2,4,6-tribromophenyl)hydrazine, (2,5-dichlorophenyl)hydrazine, (2,4,6-trichloro-3-methoxyphenyl)hydrazine and (2,3,4,5,6-pentafluoro)hydrazine for phenylhydrazine, there was prepared:
isobutyraldehyde (2,4,6-trichlorophenyl)hydrazone,
isobutyraldehyde o-tolylhydrazone,
isobutyraldehyde m-tolylhydrazone,
isobutyraldehyde p-tolylhydrazone,
isobutyraldehyde (2-bromophenyl)hydrazone,
isobutyraldehyde (4-iodophenyl)hydrazone,
isobutyraldehyde (4-trifluoromethylphenyl)hydrazone,
isobutyraldehyde (3-isopropylphenyl)hydrazone,
isobutyraldehyde (2,4,6-tribromophenyl)hydrazone,
isobutyraldehyde (2,5-dichlorophenyl)hydrazone,
isobutyraldehyde (2,4,6-trichloro-3-methoxyphenyl)hydrazone, and
isobutyraldehyde (2,3,4,5,6-pentafluoro)hydrazone, respectively.

Preparation III

Following the procedure of Preparation I, Part A, but substituting propionaldehyde, pentanaldehyde, hexanaldehyde, and heptanaldehyde for isobutyraldehyde, there is prepared propionaldehyde phenylhydrazone, pentanaldehyde phenylhydrazone, hexanaldehyde phenylhydrazone, and heptanaldehyde phenylhydrazone, respectively.

Preparation IV

Following the procedure of Preparation I, Part B, but substituting isobutyraldehyde (2,4,6-trichlorophenyl)-hydrazone for isobutyraldehyde phenylhydrazone, there was prepared isobutyryl chloride (2,4,6-trichlorophenyl)hydrazone.

Analysis:Calc'd. for $C_{10}H_{10}Cl_4N_2$: C, 40.03; H, 3.36; Cl, 47.27; N, 9.34. Found: C, 39.94; H, 3.27; Cl, 47.85; N, 9.25.

Preparation V

Pivaloyl chloride (4-chlorophenyl)hydrazone

A quantity (15.9 g.; 0.07 mole) of pivalic acid (4-chlorophenyl)hydrazide and 15.3 g. (0.0735 mole) of phosphorus pentachloride were stirred together in 100 ml. of carbon tetrachloride. The suspension was heated at the reflux temperature for 15 min., when the evolution of hydrogen chloride ceased. The reaction mixture was cooled to about 5° C. and 22.2 g. (0.236 mole) of phenol was added. After the evolution of hydrogen chloride had ceased the carbon tetrachloride was removed by evaporation under reduced pressure and the residual oil was chromatographed on 1 kg. of silica gel. Elution of the column with equal parts of benzene and technical hexane and evaporation of the solvent mixture from the eluate gave pivaloyl chloride (4-chlorophenyl)hydrazone which was recrystallized from petroleum ether. The product thus obtained had a melting point of 42° to 43° C.

Analysis: Calc'd. for $C_{11}H_{14}Cl_2N_2$: C, 53.89; H, 5.76; Cl, 28.93; N, 11.43.Found: C, 53.94; H, 5.70; Cl, 28.82; N, 11.18.

Preparation VI

Benzoic acid (2,5-dichlorophenyl)hydrazide

A mixture consisting of 17.7 g. (0.10 mole) 2,5-dichlorophenylhydrazine, 100 ml. benzene, and 22.6 g. (0.10 mole) benzoic anhydride was heated at the reflux temperature for 1½ hrs. After cooling the reaction mixture to about 25° C., it was filtered. The filtrate was evaporated to dryness, and the residue was combined with solids on the filter before dispersing the solids in 700 ml. water basified with 50% aqueous sodium hydroxide to slight alkalinity. The thus washed solids were recovered on a filter, washed with more water, and recrystallized from 225 ml. 95% ethanol. There was thus obtained 23.1 g. (82.2% yield) benzoic acid (2,5-dichlorophenyl)hydrazide having a melting point of 160.5° to 161.5° C. An analytical sample melting at 161° to 162° C. was obtained by recrystallization from 95% ethanol.

Analysis: Calc'd. for $C_{13}H_{10}Cl_2N_2O$: C, 55.53; H, 3.59; Cl, 25.22; N, 9.97. Found: C, 55.57; H, 3.91; Cl, 25.41; N, 10.07.

Preparation VII

Benzoyl chloride (2,5-dichlorophenyl)hydrazone

A quantity (16.87 g., 0.06 mole) benzoic acid (2,5-dichlorophenyl)hydrazide (Preparation VI, above) was added to a solution of 12.50 g. ((0.06 mole) phosphorus pentachloride in 50 ml. carbon tetrachloride, and the resulting suspension was allowed to react at 25° C. until evolution of hydrogen chloride gas slowed. The reaction mixture was then heated at the reflux temperature for 15 minutes, chilled in ice, and 17.8 g. (0.19 mole) phenol in 75 ml. carbon tetrachloride was added. After the reaction was completed, the carbon tetrachloride was removed by evaporation under reduced pressure at 30° to 32° C. The resulting suspension was filtered, and the filter cake was washed with 50 ml. cold methanol. Two recrystallizations from Skellysolve B gave benzoyl chloride (2,5-dichlorophenyl)hydrazone melting at 84.5° to 86° C.

Analysis: Cal'd. for $C_{13}H_9Cl_8N_2$: C, 52.12; H, 3.03; N, 9.35. Found: C, 52.59; H, 3.16; N, 9.27.

Example 1

Preparation of 1',1',2,4,6-Pentachlorobenzeneazopropane

A solution consisting of 14.8 g. (0.1 mole) propionaldehyde phenylhydrazone and 200 ml. carbon tetrachloride was cooled to minus 10° C. (−10°) and maintained at this temperature while 30 ml. chlorine (6 equivalents) was introduced into the solution. The temperature of the reaction mixture was then allowed to increase to 0° C. for 3 hrs. A sample taken at 2 hrs. indicated that the reaction was completed. After the 3 hrs., the reaction mixture was filtered to remove about 2 g. of solids, and the carbon tetrachloride was removed, from the resulting red solution, by evaporation under reduced pressure. There was thus obtained 20.8 g. of a dark red oil. A 12.0 g. sample of the gum was dissolved in 20 ml. technical hexane. About one-third of this solution was lost but the remainder was poured through a column of silica gel 50 cm. long by 5 cm. in diameter. The chromatogram was developed with 500 ml. technical hexane followed by 150 ml. of a 1:9 mixture (by volume) of benzene and technical hexane. An orange-red band migrated from a brownish band at the top of the column, and when it had reached the bottom, seven 100 ml. fractions were collected, the mixture of benzene and technical hexane being used as eluant. After combining the first five fractions and removing the solvents by evaporation under reduced pressure at 100° C., there was obtained 3.8 g. of 1',1',2,4,6-pentachlorobenzeneazopropane.

Analysis: Calc'd. for $C_9H_7Cl_5N_2$: C, 33.73; H, 2.20; Cl, 55.32; N, 8.74. Found: C, 34.15; H, 2.37; Cl, 56.87; N, 8.87.

Alternative syntheses

Following the same general procedure but using 74.0 g. (0.5 mole) propionaldehyde phenylhydrazine, 500 ml. chloroform as the solvent, and 190 ml. (4.1 mole) chlorine there was obtained 109.6 g. (68%) of 1',1',2,4,6-pentachlorobenzeneazopropane having a boiling point at 145° to 150° C. at 0.4 mm Hg. pressure.

Analysis: Calc'd. for $C_9H_7Cl_5N_2$: C, 33.73; H, 2.20; Cl, 55.32; N, 8.74. Found: C, 33.86; H, 2.25; Cl, 56.42; N, 9.11.

Following the same procedure, but using 55.0 g. (0.22 mole) propionaldehyde (2,4,6-trichlorophenyl)-hydrazone, 300 ml. benzene as the solvent, 35 ml. (0.76 mole) chlorine, and carrying out the reaction at 0° C. there was obtained 53.0 g. (75% yield) of 1',1',2,4,6-pentachlorobenzeneazopropane having a boiling point at 145° C. at a pressure of 0.4 mm Hg.

Analysis: Calc'd. for $C_9H_7Cl_5N_2$: C, 33.73; H, 2.20; Cl, 55.32; N, 8.74. Found C, 34.30; H, 2.47; Cl, 55.60; N, 8.98.

EXAMPLE 2

Preparation of 1',1',2,4,6-Pentachloro-2'-Methylbenzeneazopropane

A solution consisting of 12.0 g. (0.074 mole) isobutyraldehyde phenylhydrazone and 200 ml. carbon tetrachloride was chilled to minus 20° C. (−20°) and stirred while 26 ml. (0.56 mole) chlorine was introduced into the solution. This reaction mixture was then set aside at 0° C. for 1 hr. After removing the carbon tetrachloride by evaporation under reduced pressure, the residue thus obtained was dissolved in 150 ml. technical hexane. This solution was poured onto a column of silica gel (280 g.). The chromatogram was developed with a solvent mixture consisting of 1 part benzene and 9 parts technical hexane (by volume), and when the colored zone reached the bottom of the column, 500 ml. of eluate were collected. After removing the solvents from the eluate by evaporation under reduced pressure, there was obtained 13.4 g. of 1',1',2,4,6-pentachloro-2'-methylbenzeneazopropane as an orange oil.

Analysis: Calc'd. for $C_{10}H_9Cl_5N_2$: C, 35.91; H, 2.71; Cl, 53.00; N, 8.38. Found: C, 36.22; H, 2.74; Cl, 54.20; N, 7.93.

EXAMPLE 3

Preparation of 1',1',2,4,6-Pentachlorobenzeneazobutane

Following the procedure of Example 2, but substituting butyraldehyde phenylhydrazone for isobutyraldehyde phenylhydrazone, there was obtained 1',1',2,4,6-pentachlorobenzeneazobutane as an orange oil.

Analysis: Calc'd. for $C_{10}H_9Cl_5N_2$: C, 35.91; H, 2.71; Cl, 53.00; N, 8.38 Found: C, 35.12; H, 2.64; Cl, 54.30; N, 8.67.

EXAMPLE 4

Preparation of 1',1',2,4,6-Pentachloro-2',2'-Di-methylbenzeneazopropane

A solution consisting of 28.9 g. (0.1 mole) pivalaldehyde (2,4,6-trichlorophenyl)hydrazone and 200 ml. chloroform was chilled to minus 20° C. (−20°) and 15.0 ml. chlorine was introduced. After an interval of 1 hr. during which the reaction mixture was stirred continuously, the chloroform was removed by evaporation under reduced pressure. An oily residue was obtained that was dissolved in a mixture of benzene and technical hexane (1 part to 3 parts, by volume). This solution was applied to a 280 g. column of silica gel, and the chromatogram was developed with the same solvent mixture. When the colored band had migrated to the bottom of the column, 50 ml. fractions were collected. Fractions 3 through 8 were combined, and the solvents removed by evaporation under reduced pressure. There was thus obtained 28.0 g. of 2',2'-dimethyl-1',1',2,4,6-pentachlorobenzeneazopropane as an orange oil.

Analysis: Calc'd. for $C_{11}H_{11}Cl_5N_2$: C, 37.91; H, 3.19; Cl, 50.87; N, 8.04. Found: C, 38.16; H, 3.28; Cl, 51.63; N, 7.65.

Following the same procedure, but substituting pivaloyl chloride (4-chlorophenyl)hydrazone for pivalaldehyde (2,4,6-trichlorophenyl)hydrazone, there was prepared the same 1',1',2,4,6-pentachloro-2',2'-dimethylbenzeneazopropane.

EXAMPLE 5

Preparation of 1',1',2,4,6-Pentachlorobenzeneazohexane

Following the procedure of Example 2, but substituting hexanaldehyde phenylhydrazone for isobutyraldehyde phenylhydrazone and substituting chloroform for carbon tetrachloride as the reaction medium, there was prepared 1',1',2,4,6-pentachlorobenzeneazohexane as an orange oil.

Analysis: Calc'd. for $C_{12}H_{13}Cl_5N_2$: C, 39.76; H, 3.61; Cl, 48.90; N, 7.73. Found: C, 40.13; H, 3.67; Cl, 49.37; N, 7.46.

EXAMPLE 6

Preparation of 1',1',2,3,4,6-Hexachloro-2'-Methylbenzeneazopropane

Following the procedure of Example 2, but substituting isobutyraldehyde (2,5-dichlorophenyl)hydrazone, for isobutyraldehyde phenylhydrazone, there was prepared 1',1',2,3,4,6-hexachloro-2'-methylbenzeneazopropane as an orange oil.

Analysis: Calc'd. for $C_{10}H_8Cl_6N_2$: C, 32.55; H, 2.18; Cl, 57.67; N, 7.60. Found: C, 33.38; H, 2.55; Cl, 58.80; N, 6.92.

EXAMPLE 7

Preparation of 1',1',2,4,6-Pentachloro-2',3-Dimethylbenzeneazopropane

Following the procedure of Example 2, but substituting isobutyraldehyde m-tolylhydrazone for isobutyraldehyde phenylhydrazone and using chloroform as the organic reaction medium instead of carbon tetrachloride, there was obtained 1',1',2,4,6-pentachloro-2',3-dimethylbenzeneazopropane as an orange oil.

Analysis: Calc'd. for $C_{11}H_{11}Cl_5N_2$: C, 37.91; H, 3.18; Cl, 50.87; N, 8.04. Found: C, 38.38; H, 3.73; Cl, 52.39; N, 7.29.

EXAMPLE 8

Preparation of 1',1'-Dichloro-2,3,4,5,6-pentafluoro-2'-methylbenzeneazopropane Following the procedure of Example 2, but substituting isobutyraldehyde (2,3,4,5,6-pentafluorophenyl)hydrazone for isobutyraldehyde phenylhydrazone, there was obtained 1',1'-dichloro-2,3,4,5,6-pentafluoro-2'-methylbenzeneazopropane as an orange oil.

Analysis: Calc'd. for $C_{10}H_7Cl_2F_5N_2$: C, 37.40; H, 2.20; Cl, 22.08; F, 29.59; N, 8.73. Found: C, 38.75; H, 2.81; Cl, 24.24; F, 27.66; N, 7.99.

EXAMPLE 9

Preparation of 1',2,4,6-Tetrachloro-1'-Fluoro-2'-Methylbenzeneazopropane

A solution consisting of 9.0 g. (0.055 mole) isobutyryl chloride (2,4,6-trichlorophenyl)hydrazone and 80 ml. trichlorofluoromethane was chilled to minus 60° C. (−60°) and stirred while 8.0 g. (0.077 mole) gaseous trifluoromethyl hypofluorite was added by bubbling a stream of the gas slowly into the solution. This reaction mixture was kept at minus 60° C. for 3 hrs., and was then allowed to warm slowly to 40° C. The trichlorofluoromethane having evaporated during the warming, the residual oil thus obtained (8.1 g.) was poured onto a 280 g. column of silica gel. The chromatogram was developed with a solvent mixture consisting of equal parts benzene and technical hexane (by volume). When the colored zone had reached the bottom of the column, the eluate was collected and the solvents were removed by evaporation under reduced pressure to give 1',2,4,6-tetrachloro-1'-fluoro-2'-methylbenzeneazopropane as an orange oil.

Analysis: Calc'd. for $C_{10}H_9Cl_4FN_2$: C, 37.76; H, 2.85; Cl, 44.60; F, 5.98; N, 8.81. Found: C, 37.88; H, 3.15; Cl, 44.92; F, 5.91; N, 8.74.

Following the same procedure but substituting isobutyryl chloride (2,4-dichlorophenyl)hydrazone for isobutyryl chloride (2,4,6-trichlorophenyl)hydrazone, there was prepared 1',2,4-trichloro-1'-fluoro-2'-methylbenzeneazopropane.

EXAMPLE 10

Preparation of 1',1',2,4,6-Pentachlorobenzeneazoethane

A suspension consisting of 9.0 g. (0.05 mole) pyruvic acid 2-(phenylhydrazone) in 100 ml. chloroform was chilled to minus 20° C. (−20°) and stirred while 30 ml. (0.65 mole) chlorine was introduced into the suspension. This reaction mixture was permitted to warm up to 25° C. with condensation of the chlorine vapors in a solid carbon dioxide condenser. It was held at that temperature for 1 hr. The chloroform was removed by evaporation under reduced pressure, and the residual orange oil thus obtained was dissolved in technical hexane. The solution was poured onto a 280 g. column of silica gel, and the chromatogram was developed with a solvent mixture consisting of 1 part benzene and 9 parts technical hexane (by volume). After collecting the eluate as heretofore and removing the solvents by evaporation under reduced pressure, there was obtained 12.1 g. of 1',1',2,4,6-pentachlorobenzeneazoethane as an orange oil.

Analysis: Calc'd. for $C_8H_5Cl_5N_2$: C, 31.63; H, 1.64; Cl, 57.86; N, 9.14. Found: C, 31.57; H, 1.79; Cl, 59.49; N, 8.75.

EXAMPLE 11

Preparation of 1',1',2,3,4,5,6-Heptachlorobenzeneazoethane

A solution consisting of 20.0 g. (0.08 mole) pyruvic acid 2-[(3,5-dichlorophenyl)hydrazone] and 250 ml. chloroform was chilled to minus 40° C. and stirred while 50 ml. chlorine was introduced. After addition of the chlorine was completed, the reaction mixture was permitted to warm up to 25° C. Chlorine vapors were trapped in a condenser cooled with a mixture of solid carbon dioxide and acetone and thus returned to the reaction mixture. The reaction mixture was set aside for 6 hrs. during which time the solid carbon dioxide sublimed completely and the excess $Cl_2$ escaped. The chloroform was then removed by evaporation under reduced pressure, and the residue thus obtained was dissolved in hot methanol. The methanolic solution was chilled and a precipitate formed. The precipitate was collected on a filter and washed with methanol. The solids on the filter were recrystallized from technical hexane. There was thus obtained 15.4 g. of 1',1',2,3,4,5,6-heptachlorobenzeneazoethane having a melting point at 99° to 101° C.

Analysis:
Calc'd. for $C_8H_3Cl_7N_2$: C, 25.59; H, 0.80; N, 7.46. Found: C, 25.69; H, 1.00; N, 7.37.

EXAMPLE 12

Following the procedure of Example 4, but substituting heptanaldehyde (2,4,6-trichlorophenyl)hydrazone, octanaldehyde (2,4,6-trichlorophenyl)hydrazone, and 2-ethylhexanaldehyde (2,4,6-trichlorophenyl)hydrazone for pivalaldehyde (2,4,6-trichlorophenyl)hydrazone there was prepared.
1',1',2,4,6-pentachlorobenzeneazoheptane,
1',1',2,4,6-pentachlorobenzeneazooctane, and
1',1',2,4,6-pentachloro-2'-ethylbenzeneazohexane, respectively.

EXAMPLE 13

Following the procedure of Example 9, but substituting cyclopropane carbonyl chloride (2,4,6-trichlorophenyl)hydrazone, cyclobutane carbonyl chloride (2,4,6-trichlorophenyl)hydrazone, cyclopentane carbonyl chloride (2,4,6-trichlorophenyl)hydrazone, cyclohexane carbonyl chloride (2,4,6-trichlorophenyl)hydrazone, cycloheptane carbonyl chloride (2,4,6-trichlorophenyl)hydrazone, and 3-methylcyclohexane carbonyl chloride (2,4,6-trichlorophenyl)hydrazone for isobutyryl chloride (2,4,6-trichlorophenyl)hydrazone, there is prepared:
1',2,4,6-tetrachloro-1'-cyclopropyl-1'-fluorobenzeneazomethane,
1',2,4,6-tetrachloro-1'-cyclobutyl-1'-fluorobenzeneazomethane,
1',2,4,6-tetrachloro-1'-cyclopentyl-1'-fluorobenzeneazomethane,
1',2,4,6-tetrachloro-1'-cyclohexyl-1'-fluorobenzeneazomethane,
1',2,4,6-tetrachloro-1'-cycloheptyl-1'-fluorobenzeneazomethane, and 1',2,4,6-tetrachloro-1'-(3-methylcyclohexyl)-1'-fluorobenzeneazomethane, respectively.

EXAMPLE 14

Following the procedure of Example 2, but substituting trifluoroacetaldehyde phenylhydrazone, trichloroacetaldehyde phenylhydrazone, chloroacetaldehyde phenylhydrazone, glycolaldehyde phenylhydrazone, 3,4-diiodobutyraldehyde phenylhydrazone, 3-methoxypropionaldehyde phenylhydrazone, 7-methoxyheptanaldehyde phenylhydrazone, 3,3-dibromooctanaldehyde phenylhydrazone, and 7-hydroxyoctanaldehyde phenylhydrazone for isobutyraldehyde phenylhydrazone, there was prepared:
1',1',2,4,6-pentachloro-2',2',2'-trifluorobenzeneazoethane,
1',1',2',2',2,4,6-octachlorobenzeneazoethane,
1',1',2',2,4,6-hexachlorobenzeneazoethane,
1',1',2,4,6-pentachloro-2'-hydroxybenzeneazoethane,
1',1',2,4,6pentachloro-3',4'-diiodobenzeneazobutane,
1',1',2,4,6-pentachloro-3'-methoxybenzeneazopropane,
1',1',2,4,6-pentachloro-7'-methoxybenzeneazoheptane,
3',3'-dibromo-1',1',2,4,6-pentachlorobenzeneazooctane, and
1',1',2,4,6-pentachloro-7'-hydroxybenzeneazooctane, respectively.

EXAMPLE 15

Following the procedure of Example 11, but substituting pyruvic acid 2-[(2,5-xylyl)hydrazone], pyruvic acid 2-[(3,5-diethylphenyl)hydrazone], pyruvic acid 2-[(2,3-diiodophenyl)hydrazone], pyruvic acid 2-[(α,α,α-trifluoro-m-tolyl)hydrazone], pyruvic acid 2-[(α,α,α-trifluoro-p-tolyl)hydrazone], pyruvic acid 2-[(4-methoxy-m-tolyl)hydrazone], pyruvic acid 2-[(p-butoxyphenyl)hydrazone], pyruvic acid 2-[(3,5-diisobutylphenyl)hydrazone], pyruvic acid 2-[(m-isopropylphenyl)hydrazone], pyruvic acid 2-{[2-(2fluoroethyl)phenyl-]hydrazone}, pyruvic acid 2-{[3-(2,2-difluoropropyl) phenyl]hydrazone}, pyruvic acid 2-[(4-fluorophenyl)-hydrazone], pyruvic acid 2-[(4-bromophenyl)hydrazone] for pyruvic acid 2-[(3,5-dichlorophenyl)hydrazone], there was prepared:
1',1',2,4-tetrachloro-3,6-dimethylbenzeneazoethane,
1',1',2,4,6-pentachloro-3,5-diethylbenzeneazoethane,
1',1',2,4-tetrachloro-5,6-diiodobenzeneazoethane,
1',1',2,4,6-pentachloro-(α,α,α-trifluoro-m-tolyl)azoethane,
1',1',2,6-tetrachloro-(α,α,α-trifluoro-p-tolyl)azoethane,
1',1',2,6-tetrachloro-(4-methoxy-m-tolyl)azoethane,
4-butoxy-1',1',2,6-tetrachlorobenzeneazoethane,
1',1',2,4,6-pentachloro-3,5-diisobutylbenzeneazoethane,
1',1',2,4,6-pentachloro-3-isopropylbenzeneazoethane,
1',1',2,4-tetrachloro-6-(2-fluoroethyl)benzeneazoethane,
1',1',2,4,6-pentachloro-3-(2,2-difluoropropyl)benzeneazoethane,
1',1',2,6-tetrachloro-4-fluorobenzeneazoethane, and
4-bromo-1',1',2,6-tetrachlorobenzeneazoethane, respectively.

EXAMPLE 16

Following the procedure of Example 1, but substituting bromine for chlorine and separately substituting pivaloyl chloride (o-tolyl)hydrazone and pivaloyl chloride phenylhydrazone for propionaldehyde phenylhydrazone, there was prepared:
1',4,6-tribromo-1'-chloro-2,2',2'-trimethylbenzeneazopropane,
1',2,4,6-tetrabromo-1'-chloro-2',2'-dimethylbenzeneazopropane, respectively.

EXAMPLE 17

Following the procedure of Example 9, but substituting isobutyraldehyde (2,4,6-trichlorophenyl)hydrazone for isobutyryl chloride (2,4,6-trichlorophenyl)hydrazone, there is prepared 2,4,6-trichloro-1',1'-difluoro-2'-methylbenzeneazopropane.

EXAMPLE 18

Following the procedure of Example 9, but substituting acetyl chloride (3-butyl-2,4,6-trichlorophenyl)hydrazone, propionyl chloride (2,3,4,6-tetrachlorophenyl)hydrazone, pivaloyl bromide (2,4,6-trichlorophenyl)hydrazone, pivaloyl chloride [2-chloro-4,6-bis(trifluoromethyl)phenyl]hydrazone, butyryl chloride (2,4,6-tribromophenyl)hydrazone, and valeryl chloride (2,4,6-trichlorophenyl)hydrazone, there were prepared:
3-butyl-1',2,4,6-tetrachloro-1'-fluorobenzeneazoethane,
1',2,3,4,6-pentachloro-1'-fluorobenzeneazopropane,
1'-bromo-2,4,6-trichloro-1'-fluoro-2'',2'-dimethylbenzeneazopropane,
1',2-dichloro-1'-fluoro-2',2'-dimethyl-4,6-bis(trifluoromethyl)benzeneazopropane,
2,4,6-tribromo-1'-chloro-1'-fluorobenzeneazobutane, and 1',2,4,6-tetrachloro-1'-fluorobenzeneazopentane, respectively.

EXAMPLE 19

Following the procedure of Example 2, but substituting isobutyraldehyde o-tolylhydrazone, isobutyraldehyde p-tolylhydrazone, isobutyraldehyde (2-bromophenyl)hydrazone, isobutyraldehyde (4-iodophenyl)hydrazone, isobutyraldehyde (4-trifluoromethylphenyl)hydrazone, isobutyraldehyde (3-isopropylphenyl)hydrazone, isobutyraldehyde (2,4,6-tribromophenyl)hydrazone, and isobutyraldehyde (2,4,6-trichloro-3-methoxyphenyl)hydrazone for isobutyraldehyde phenylhydrazone, there were prepared:

1',1',2,4-tetrachloro-2',6-dimethylbenzeneazopropane,
1',1',2,6-tetrachloro-2',4-dimethylbenzeneazopropane,
2-bromo-1',1',4,6-tetrachloro-2'-methylbenzeneazopropane,
1',1',2,6-tetrachloro-4-iodo-2'-methylbenzeneazopropane,
1',1',2,6-tetrachloro-2'-methyl-4-(trifluoromethyl)-benzeneazopropane,
1',1',2,4,6-pentachloro-3-isopropyl-2'-methylbenzeneazopropane,
2,4,6-tribromo-1',1'-dichloro-2'-methylbenzeneazopropane, and
1',1',2,4,6-pentachloro-3-methoxy-2'-methylbenzeneazopropane, respectively.

EXAMPLE 20

Preparation of
1',1',2,4,6-Pentachloro-1'-Phenylbenzeneazomethane

Chlorine [10.6 ml. (0.23 mole)] was added to a solution of 16.7 g. (0.05 mole) benzoyl chloride (2,4,6-trichlorophenyl)hydrazone in 200 ml. carbon tetrachloride. The reaction mixture was allowed to stand at 25° C. for 18 hrs. The solvent was then removed by evaporation under reduced pressure to give a dark red oil. A portion of this oil (6.5 g.) was dissolved in a solvent mixture consisting of equal parts benzene and technical hexane. This solution was poured through a column of 80 g. silica gel. The chromatogram was developed using the same solvent mixture and the fractions containing the orange product were pooled. After removing the solvents by evaporation under reduced pressure, there was obtained 5.0 g. of 1',1',2,4,6-pentachloro-1'-phenylbenzeneazomethane as an orange-red oil.

Analysis: Calc'd. for $C_{13}H_7Cl_5N_2$: C, 42.37; H, 1.92; Cl, 48.11; N, 7.60. Found: C, 42.44; H, 2.25; Cl, 49.20; N, 7.04.

Following the same procedure, but substituting benzoyl chloride o-tolylhydrazone, benzoyl chloride -(2,4-dibromophenyl)hydrazone, -(2,5-dichlorophenyl)hydrazone, -(2,4,6-trichloro-3-isopropylphenyl)hydrazone, -(2,6-dibromo-4-butylphenyl)hydrazone, -(2-bromo-5-iodophenyl)hydrazone, -(2,4,6-trichloro-m-anisyl)hydrazone, -(2-trifluoromethylphenyl)hydrazone, and benzoyl chloride (4-trifluoromethyl)phenylhydrazone for benzoyl chloride (2,4,6-trichlorophenyl)hydrazone there is prepared:

1',1',2,4-tetrachloro-6-methyl-1'-phenylbenzeneazomethane,
2,4-dibromo-1',1',6-trichloro-1'-phenylbenzeneazomethane,
1',1',2,3,4,6-hexachloro-1'-phenylbenzeneazomethane,
1',1',2,4,6-pentachloro-1'-phenyl-3-isopropylbenzeneazomethane,
2,6-dibromo-4-butyl-1',1'-dichloro-1'-phenylbenzeneazomethane,
2-bromo-1',1',4,6-tetrachloro-5-iodo-1'-phenylbenzeneazomethane,
1',1',2,4,6-pentachloro-3-methoxy-1'-phenylbenzeneazomethane,
1',1',2,4-tetrachloro-6-trifluoromethyl-1'-phenylbenzeneazomethane, and
1',1',2,6-tetrachloro-4-trifluoromethyl-1'-phenylbenzeneazomethane, respectively.

Following the same procedure but substituting p-bromobenzoyl chloride phenylhydrazone, m-chlorobenzoyl chloride phenylhydrazone, 3,4-dichlorobenzoyl chloride phenylhydrazone, o-chlorobenzoyl chloride (2-trifluoromethylphenyl)-hydrazone, and p-chlorobenzoyl chloride (2,4,6-tribromo-m-tolyl)hydrazone for benzoyl chloride (2,4,6-trichlorophenyl)-hydrazone there is prepared:

1',1',2,4,6-pentachloro-1'-(p-bromophenyl)benzeneazomethane,
1',1',2,4,6-pentachloro-1'-(m-chlorophenyl)benzeneazomethane,
1',1',2,4,6-pentachloro-1'-(3,4-dichlorophenyl)benzeneazomethane,
1',1',2,4-tetrachloro-6-trifluoromethyl-1'-(o-chlorophenyl)benzeneazomethane, and
2,4,6-tribromo-1',1'-dichloro-3-methyl-1'-(p-chlorophenyl)benzeneazomethane, respectively.

The new 1'-variable-1',1'-dihalo-halobenzeneazomethanes of this invention (compounds according to Formula 1) are active against both grassy and broad-leafed weeds. Corn is not injured. Some known susceptible weeds include crab-grasses (e.g., Digitaria sanguinalis and Digitaria ischaemum), yellow foxtail (Setaria lutescens), bindweed (Convolvulus arvensis L.), Johnsongrass (Sorghum halepense (L.) Pres.), buckhorn plantain (Plantago lanceolata L.), and curly dock (Rumex crispus). Numerous other weeds are also controlled by application of the new compounds.

Having now discovered the herbicidal activity of the 1'-variable-1',1'-dihalo-halobenzeneazomethanes of Formula 1, there are certain classes of these compounds that possess exceptional qualities and are preferred. Illustratively, the compounds of Formula I wherein R is alkyl, one X is chlorine, and $R_1$ and $R_2$ are chlorine are preferred compounds of the invention. Among these compounds, the 1',1',2,4,6-pentachlorobenzeneazoalkanes are particularly preferred, especially 1',1',2,4,6-pentachlorobenzeneazopropane and 1',1',2,4,6-pentachloro-2',3-dimethylbenzeneazopropane. Other preferred compounds of the invention include, e.g., 1',1',2,4,6-pentachlorobenzeneazoethane, 1',1',2,3,4,5,6-heptachlorobenzeneazoethane, 1',1',2,4,6-pentachlorobenzeneazobutane, 1',1',2,4,6-pentachloro-2'-methylbenzeneazopropane, 1',1',2,4,6-pentachloro-2',2'-dimethylbenzeneazopropane, 1',1',2,4,6-pentachlorobenzeneazohexane, 1',1',2,3,4,5-hexachloro-2'-methylbenzeneazopropane.

The 1'-variable-1',1'-dihalo-halobenzeneazomethanes can be applied singly for control of weeds, but if desired a mixture of the compounds can be used. The compounds can be applied in their pure form, as technical grade compounds, as crude mixtures of a compound or compounds or as improved agronomic formulations. Such improved formulations are characterized by the presence of adjuvants that promote effective use of the active ingredient compounds and contribute toward economical practice of the invention. In some situations a solvent might be desirable, in other instances a bodying material such as a pulverulent solid might be desirable. Such liquids and solids for diluting the active compounds are termed carriers. In still other situations wetting or dispersing agents, stickers and spreaders, or even other active ingredients might be desired.

Agronomic formulations in accordance with the objectives of the inventions include, for example, solutions, liquid suspensions, emulsions, creams, pastes, wettable powders, dusts, emulsifiable concentrates, granulars, and impregnated elastomeric strips, ribbons, or blocks. In general, the active component is preferably in a dispersed or readily dispersible form. Dispersibility promotes thorough and uniform coverage of any objectionable area of weeds so that the desired control is realized.

When selective weed control in a crop area or turf is desired, a non-phytotoxic carrier is preferred. In this way the crop plants or desirable grasses are not injured, but the weeds are selectively killed by the 1'-variable-1',1'-dihalo-halobenzeneazomethanes active ingredient. Water is an ubiquitous non-phytotoxic carrier. Certain non-phytotoxic crop oils can be used in small amounts of about 1 gal. per acre. Solids ordinarily employed in herbicidal formulations are not phytotoxic. On the other hand, when total control of vegetation is desired, a phytotoxic carrier can be chosen. Appropriate phytotoxic carriers are, e.g., high-boiling petroleum fractions and tetrachlorethane.

The efficacy of 1'-variable-1',1'-dihalo-halobenzeneazomethanes as herbicides is of high order, and the compounds can be applied at relatively low rates per acre for controlling growth of weed plants, e.g., germinating weed seedlings. Illustratively, the compounds 1',1',2,4,6-pentachlorobenzeneazopropane and 1',-1',2,4,6-pentachloro-2',3-dimethylbenzeneazopropane gave complete or substantially complete suppression of Bermuda grass (Cynodon dactylon) when applied at rates of 6 lbs. and 3 lbs. per acre. In general, rates of application of about 1.0 to about 15 lbs. per acre are efficacious under usual conditions, depending upon the particular circumstances such as type of soil, amount of rainfall or irrigation, and the most prevalent susceptible weeds. At the high rate of application, e.g., at 20 to 50 lbs. per acre the compound acts as a soil sterilant.

Illustratively, excellent control of weeds in rice fields has been obtained, without significant damage to the rice plants, using concentrations of 1'-variable-1',1'-dihalo-halobenzeneazomethanes ranging from about 1000 ppm (parts per million) to about 5000 ppm applied at the rates of about 1 lb. to about 4.0 lbs. per acre. In general, a desired rate of application can be achieved by distributing, over the area to be treated, an aqueous spray formulation in accordance with the invention, containing from about 700 ppm to about 30,000 ppm of active ingredient. It will be understood, of course, that a choice of concentration of active ingredient depends upon the method of application as well as the type of formulation and the degree of herbicidal control desired. In general, concentration is not critical within the range indicated since an effective quantity of active ingredient can be applied to a given area by applying greater quantities of a low concentration than of a higher concentration. The concentration of active ingredient in the dispersible powder and emulsifiable concentrates from which the aqueous spray formulations are prepared can be as high as 99.5% by weight. The concentration of active ingredient in the dust and granular formulations of the invention can vary from about 0.25% to about 80% or more, but advantageously is of the order of 0.50% to 20%.

The granular formulations of this invention are prepared with about 0.25% to about 80%, preferably 0.50% to 20% by weight, of active ingredient and a granular carrier, for example, heat expanded vermiculite, heat expanded perlite, pyrophyllite, or attapulgite. The active ingredient can be dissolved in a volatile solvent such as methylene chloride, acetone, and the like, and sprayed on the granular carrier as it is mixed and tumbled. The granules are then dried. The granular carrier can range in particle size from about 10 to about 60 mesh, preferably about 30 to 60 mesh.

The herbicidal dust compositions of the invention are prepared by intimate admixture of from about 0.25% to about 80% by weight, preferably 0.50% to 20% of the active ingredient with a solid pulverulent carrier which maintains the composition in a dry, free-flowing condition. The herbicidal dusts of the invention can be prepared by admixing the compound with a solid diluent and then milling. Preferably, however, the active ingredient is dissolved in a volatile organic solvent, of the kinds indicated above, and then sprayed on the solid carrier so as to assure thorough distribution. The mixture is then dried and milled to the desired size, e.g., less than about 60 microns.

Solid carriers that can be used in the dust compositions of the invention include the natural clays such as China clay and bentonite, minerals in the natural state such as talc, pyrophyllite, quartz, diatomaceous earth, fuller's earth, chalk, and rock phosphate, and the chemically modified minerals such as washed bentonite, precipitated calcium phosphate, precipitated calcium carbonate, precipitated calcium silicate, and colloidal silica. The solid diluents which can be employed in the compositions also include solid, compounded fertilizers. Such solid compositions can be applied to vegetation in the form of dusts by the use of conventional equipment.

A preferred compositions, in accordance with the invention, is a dispersible powder which is prepared by incorporating a surfactant in a dust composition prepared as described above. Such a dispersible powder can be dispersed in water to a desired concentration and applied to vegetation by conventional spray equiment. Conveniently, the dispersible powders are formulated with higher concentrations of active ingredient than the dust compositions, for example, up to about 90%, preferably about 10% to 80%. Surfactants useful in preparing such dispersible powder compositions include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyester alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. A preferred class of surfactants includes blends of sulfonated oils and polyalcohol carboxylic acids esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N$_4$S). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powders can be formulated with a mixture of surfactants of the types indicated if desired.

Anionic and nonionic surfactants are preferred. Appropriate cationic surfactants are the calcium salts of myristyl benzenesulfonic acid and lauryl benzenesulfonic acid. An appropriate nonionic surfactant is the oleate ester of a polyoxyethylene glycol having molecular weight about 350–500. Other surfactants as described by J. McCutcheon, *Soap and Chemical Specialties*, (Dec. 1957) and (Jan., Feb., March, and April, 1958) are useful.

A suitable dispersible powder formulation is obtained by blending and milling 235 lbs. of Georgia Clay, 5.5. lbs. of isooctylphenoxy polyethoxy ethanol (Triton X-100) as a wetting agent, 9.5 lbs. of a polymerized sodium salt of substituted benzoid long-chain sulfonic acid (Daxad 27) as a dispersing agent, and 250 lbs. of the active ingredient. The resulting formulation has the following percentage composition (parts herein are by weight unless otherwise specified).

| | |
|---|---|
| Active ingredient | 50% |
| Isooctylphenoxy polyethoxy ethanol | 1.1% |
| Polymerized Sodium salt of substituted benzoid long-chain sulfonic acid | 1.9% |
| Georgia Clay | 47% |

This formulation, when dispersed in water at the rate of 10 lbs. per 100 gals., gives a spray formulation containing about 0.6% (6000 ppm) active ingredient which can be applied to soil, plant growth media, growing plants, e.g., turf at the rate of 40 gals. per acre to give a total application of active ingredient of 2 lbs. per acre.

The compounds of this invention can be applied to soil, plants, plant growth media, growing plants, e.g., turf in aqueous sprays without a solid carrier. However, since the compounds themselves are relatively insoluble in water they are preferably dissolved in a suitable inert organic solvent carrier. Advantageously, the solvent carrier is immiscible with water so that an emulsion of the solvent carrier in water can be prepared. If, for example, a water-miscible solvent carrier such as acetone is used the solvent carrier will dissolve in the water and any excess according to Formula I will be thrown out of solution. In an emulsion, the solvent phase is dispersed in the water phase and the active ingredient is held in solution in the dispersed phase. In this way, uniform distribution of active ingredient with an aqueous spray can be achieved.

A solvent carrier in which the compounds are highly soluble is desirable so that relatively high concentrations of active ingredient can be obtained. Sometimes, one or more solvent carriers with or without a cosolvent can be used in order to obtain concentrated solutions of the active ingredient. The main consideration being to employ a water-immiscible solvent for the active ingredient that will hold the compound in solution over the range of concentrations useful for preventing germination of undesired seeds and controlling growth of plants.

The emulsifiable concentrates of the invention are prepared by dissolving the active ingredient and a surfactant in a substantially water-immiscible solvent carrier (i.e., a solvent carrier which is soluble in water to the extent of less than 2.5% by volume at temperatures of the order of 20° to 30+ C.), for example, cyclohexanone, methyl propyl ketone, summer oils, ethylene dichloride, aromatic hydrocarbons such as benzene, toluene, and xylene, and high-boiling petroleum hydrocarbons such as heavy aromatic naphtha kerosene, diesel oil, and the like. If desired, a cosolvent such as methyl ethyl ketone, acetone, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed if desired.

Advantageously, the concentration of active ingredient in the emulsifiable concentrates can range from about 5% to about 50% by weight, preferably from about 10% to 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm of active ingredient. In the same manner, more concentrated solutions of active ingredient can be prepared.

The concentrate compositions of the invention which are intended for use in the form of aqueous dispersions or emulsions can also comprise a humectant, that is to say, an agent which will delay the drying of the composition in contact with material to which it has been applied. Suitable humectants include solubilized lignins, such as calcium lignosulfonate, and the like.

Further in accordance with this invention, certain formulations of 1'-variable-1',1'-dihalo-halobenzeneazomethanes with oil are particularly efficacious, and herbicidal action of the compound is improved. A petroleum oil having a viscosity rating in the range of 70–100 secs. (Saybolt) is satisfactory. Such non-phytotoxic crop oils are beneficial when used at the rate of about 1 to 2 gals. per acre. They seem to promote penetration of the herbicide into the weeds or perhaps predispose the weed plant surface to penetration.

Advantageously, a 50% wettable powder of the herbicidal active ingredient is mixed with about 38 gals. water and 2 gals. oil for spray application. Alternatively, about 2 gals. oil and a 50% wettable powder are premixed and then dispersed in about 38 gals. water for spray application. In field tests, oil formulations of the foregoing type have given improved herbicidal action.

The rates of application to soils, plant growth media, growing plants, e.g., turf to be protected from noxious weeds will depend upon the species of vegetation to be controlled, the presence or absence of desirable species, the season of year at which treatment is undertaken, and the method and efficiency of application. In general, selective herbicidal activity is obtained when the active compounds are applied at the rate of about 1.0 to about 15 lbs. per acre, preferably at the rate of about 1.0 to about 8 lbs. per acre.

The formulations containing 1'-variable-1',1'-dihalohalobenzeneazomethanes can be applied to soil, plant growth media, growing plants, e.g., turf, by conventional methods. For example, an area of soil can be treated prior to or after seeding by spraying wettable powder suspensions, emulsions or solutions from boom-type power sprayers or from hand-operated knapsack sprayers. Dusts can be applied by power dusters, or by hand-operated dusters. Dusts and granular formulations can also be applied at the time of seeding in bands spanning in seeded rows.

The following examples are illustrative of the process and products of the present invention, but are not to be construed as limiting.

EXAMPLE 21

A dispersible powder concentrate having the following percentage composition:

| | |
|---|---|
| 1',1',2,3,4,5,6-heptachloro-benzeneazoethane | 45.8% |
| Polymerized sodium salt of substituted benzoid long-chain sulfonic acid (Daxad 27) | 9.2% |
| Kaolinite | 45.0% | was prepared by mixing 250 g. of 1.40 ,1',2,3,4,5,6-heptachlorobenzeneazoethane, 50 g. of a polymerized sodium salt of substituted benzoid long-chain sulfonic acid (Daxad 27), and 245 g. of kaolinite. The mixture was milled to a particle size averaging 5 to 30 microns. It was suspended in 10 gals. of water, giving an aqueous spray containing about 6500 parts per million of active ingredient.

EXAMPLE 22

A fine granular formulation having the following percentage composition:

| | |
|---|---|
| 1',1',2,4,6-pentachloro-2',3-dimethylbenzene-azopropane | 3.7% |
| Vermiculite (30/60 mesh) | 96.3% | was prepared by spraying a solution of 220 g. of 1',-1',2,4,6-pentachloro-2',3-dimethylbenzeneazopropane in 1000 ml. of methylene chloride onto 5780 g. of vermiculite (30 to 60 mesh) while the vermiculite was being tumbled and stirred so as to assure even distribution. The methylene chloride was then evaporated, leaving the active compound adsorbed on the vermiculite, and the vermiculite was pulverized.

EXAMPLE 23

An emulsifiable concentrate having the following percentage composition:

| | |
|---|---|
| 1',1',2,4,6-pentachloro-benzeneazoethane | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of 1',1',2,4,6-pentachlorobenzeneazoethane, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 lbs. of the concentrate mixed with 10 gals. of water gave a spray emulsion containing about 11,000 ppm of active ingredient.

EXAMPLE 24

An emulsifiable concentrate having the following percentage composition:

| | |
|---|---|
| 1',1',2,4,6-pentachloro-2',2'-dimethylbenzene-azopropane | 40.0% |
| Technical alkyl naphthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanols (Triton X-151) | 5.0% | was prepared by mixing 40.0 lbs. of 1',1',2,4,6-pentachloro-2',2'-diemthylbenzeneazopropane, 13.7 lbs. of Velsicol AR50, 12.3 lbs. of xylene, 11.3 lbs. of acetone, 17.7 lbs. of ethylene dichloride, and 5.0 lbs. of Triton X-151.

1.67 lbs. of the concentrate mixed with 10 gals. of water gave a spray emulsion containing about 8,000 ppm of active ingredient.

EXAMPLE 25

A dispersible powder concentrate having the following percentage composition:

| | |
|---|---|
| 1',1',2,4,6-pentachloro-benzeneazohexane | 50% |
| Kaolinite clay (finely divided) | 46% |
| Sodium salt of condensed mononaphthalene sulfonic acid (Lomar D) | 4% | was prepared by mixing 50 g. of 1',1',2,4,6-pentachlorobenzeneazohexane, 46 g. of the kaolinite clay, and 4 g. of Lomar D. The mixture was milled to an average particle size of 5 to 30 microns.

EXAMPLE 26

A granular formulation having the following percentage composition:

| | |
|---|---|
| 1',1',2,4,6-pentachloro-2'-methylbenzeneazo-propane | 1% |
| Pyrophyllite (30/60 mesh) | 99% | was prepared by dissolving 1.0 lb. of 1',1',2,4,6-pentachloro-2'-methylbenzeneazopropane in 10.0 l. of ethylene dichloride and spraying the solution on 99.0 lbs. of pyrophyllite. The granules were dried and then packaged for use.

EXAMPLE 27

In a test, various amounts of 1',1',2,4,6-pentachloro-2',3-dimethylbenzeneazopropane were applied to substantially uniform volumes of a pond compartmented by plastic partitions. Each compartment had 20 sq. ft. of surface area and water depth was 3 ft. Each had about the same association of aquatic plant life, particularly plankton and filamentous algae. The compound was applied by under water injection in amounts calculated to obtain concentrations of 2 ppm, 1 ppm, 0.5 ppm, and 0.25 ppm.

After 6 weeks, during midsummer, the control of plankton and filamentous algae was observed to be 100%, 90%, 30%, and imperceptible, respectively.

I claim:

1. A 1'-variable-1',1'-dihalo-halobenzeneazomethane of the structural formula

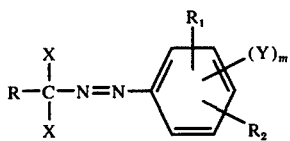

wherein R is hydrogen; alkyl of from 1 to 7 carbon atoms, inclusive; cycloalkyl of from 3 to 7 carbon atoms, inclusive; haloalkyl of from 1 to 7 carbon atoms, inclusive; halocycloalkyl of from 3 to 7 carbon atoms, inclusive; alkoxyalkyl of from 2 to 8 carbon atoms, inclusive; hydroxyalkyl of from 1 to 7 carbon atoms, inclusive; and phenyl optionally having 1, 2, or 3 substituents, e.g., halogen atoms, lower-alkyl of from 1 to 4 carbon atoms, inclusive, halolower-alkyl of from 1 to 4 carbon atoms, inclusive, and lower-alkoxy of from 1 to 4 carbon atoms, inclusive; the X's are independently bromine, chlorine, or fluorine; m is an integer 0, 1, 2, or 3; and $R_1$, $R_2$, and Y are independently halogen, lower-alkyl of from 1 to 4 carbon atoms, inclusive; halolower-alkyl of from 1 to 4 carbon atoms, inclusive; or lower-alkoxy of from 1 to 4 carbon atoms, inclusive; providing however, that at least one $R_1$ and $R_2$ is halogen, and that the sum of the carbon atoms in substituents $R_1$, $R_2$, and Y may not be more than 15.

2. A 1'-alkyl-1',1'-halobenzeneazomethane according to claim 1.

3. A 1',1'-dichloro-halobenzeneazoalkane according to claim 2.

4. A 1',1'-dichloro-chlorobenzeneazopropane according to claim 3.

5. The compound according to claim 4, 1',1',2,4,6-pentachlorobenzeneazopropane.

6. The compound according to claim 4, 1',1',2,4,6-pentachloro-2'-methylbenzeneazopropane.

7. The compound according to claim 4, 1',1',2,4,6-pentachloro-2',2'-dimethylbenzeneazopropane.

8. The compound according to claim 4, 1',1',2,3,4,6-hexachloro-2'-methylbenzeneazopropane.

9. The compound according to claim 4, 1',1',2,4,6-pentachloro-2',3-dimethylbenzeneazopropane.

10. A 1',1'-dichloro-fluorobenzeneazoalkane according to claim 3.

11. The compound according to claim 10, 1',1'-dichloro 2,3,4,5,6-pentafluoro-2'-methylbenzeneazopropane.

12. A 1',1'-dichloro-chlorobenzeneazoethane according to claim 3.

13. The compound according to claim 12, 1',1',2,4,6-pentachlorobenzeneazoethane.

14. The compound according to claim 12, 1',1',2,3,4,5,6-heptachlorobenzeneazoethane.

15. A 1'-chloro-1'-halo-halobenzeneazoalkane according to claim 2.

16. A 1'-chloro-1'-fluoro-chlorobenzenealkane according to claim 15.

17. The compound according to claim 16, 1',2,4,6-tetrachloro-1'-fluoro-2'-methylbenzeneazopropane.

18. The compound according to claim 3, 1',1',2,4,6-pentachlorobenzeneazobutane.

19. The compound according to claim 3, 1',1',2,4,6-pentachlorobenzeneazohexane.

* * * * *